(12) United States Patent
Byington et al.

(10) Patent No.: US 7,783,100 B2
(45) Date of Patent: Aug. 24, 2010

(54) METHOD AND APPARATUS FOR INSPECTING AND ANALYZING WELDED STRUCTURES

(75) Inventors: Stephen Byington, Lawrenceburg, KY (US); Keith Carpenter, Nicholasville, KY (US)

(73) Assignee: Topy America, Inc., Frankfort, KY (US)

( * ) Notice: Subject to any disclaimer, the term of this patent is extended or adjusted under 35 U.S.C. 154(b) by 825 days.

(21) Appl. No.: 11/726,228

(22) Filed: Mar. 21, 2007

(65) Prior Publication Data

US 2008/0234960 A1 Sep. 25, 2008

(51) Int. Cl.
*G06K 9/00* (2006.01)

(52) U.S. Cl. .......................... 382/141; 382/152; 702/35; 348/86; 348/125; 700/166; 700/212

(58) Field of Classification Search ................. 382/141, 382/152; 702/35; 348/86, 125; 700/166, 700/212
See application file for complete search history.

(56) References Cited

U.S. PATENT DOCUMENTS

| | | | |
|---|---|---|---|
| 4,501,950 A | 2/1985 | Richardson | |
| 4,877,940 A | 10/1989 | Bangs | |
| 5,293,324 A | * 3/1994 | Tokura | ....................... 382/141 |
| 5,293,687 A | 3/1994 | Willoughby, Jr. | |
| 5,380,978 A | 1/1995 | Pryor | |
| 5,533,146 A | 7/1996 | Iwai | |
| 5,603,447 A | 2/1997 | Shalosky | |
| 5,619,587 A | 4/1997 | Willoughby, Jr. | |
| 6,204,469 B1 | 3/2001 | Fields, Jr. | |
| 6,261,701 B1 | 7/2001 | Fields, Jr. | |
| 6,479,786 B1 | 11/2002 | Fields, Jr. | |
| 6,547,123 B2 | 4/2003 | Kemmerer | |
| 6,585,146 B2 | 7/2003 | Shepard | |
| 6,949,005 B1 | 9/2005 | Larsen | |
| 2002/0134820 A1 | 9/2002 | Kemmerer | |
| 2003/0165180 A1 | 9/2003 | Weerasinghe | |
| 2006/0159331 A1 | 7/2006 | Kubo | |

* cited by examiner

*Primary Examiner*—John B Strege
(74) *Attorney, Agent, or Firm*—Stoll Keenon Ogden PLLC; David J. Clement; Justin M. Tromp

(57) ABSTRACT

An apparatus and method for inspecting and analyzing welded structures includes a laser for directing at least one beam of light at a weld bead to define at least one visible profile line; a camera directed at the weld bead for capturing an image of the at least one profile line and generating a usable image signal based on the image; and a preprogrammed microprocessor assembly configured for receiving the usable image signal and processing the signal as an image to determine a dimension of the weld bead defined along the at least one profile line and comparing the dimension of the weld bead with a predetermined dimension set point to determine the quality of the weld bead.

22 Claims, 5 Drawing Sheets

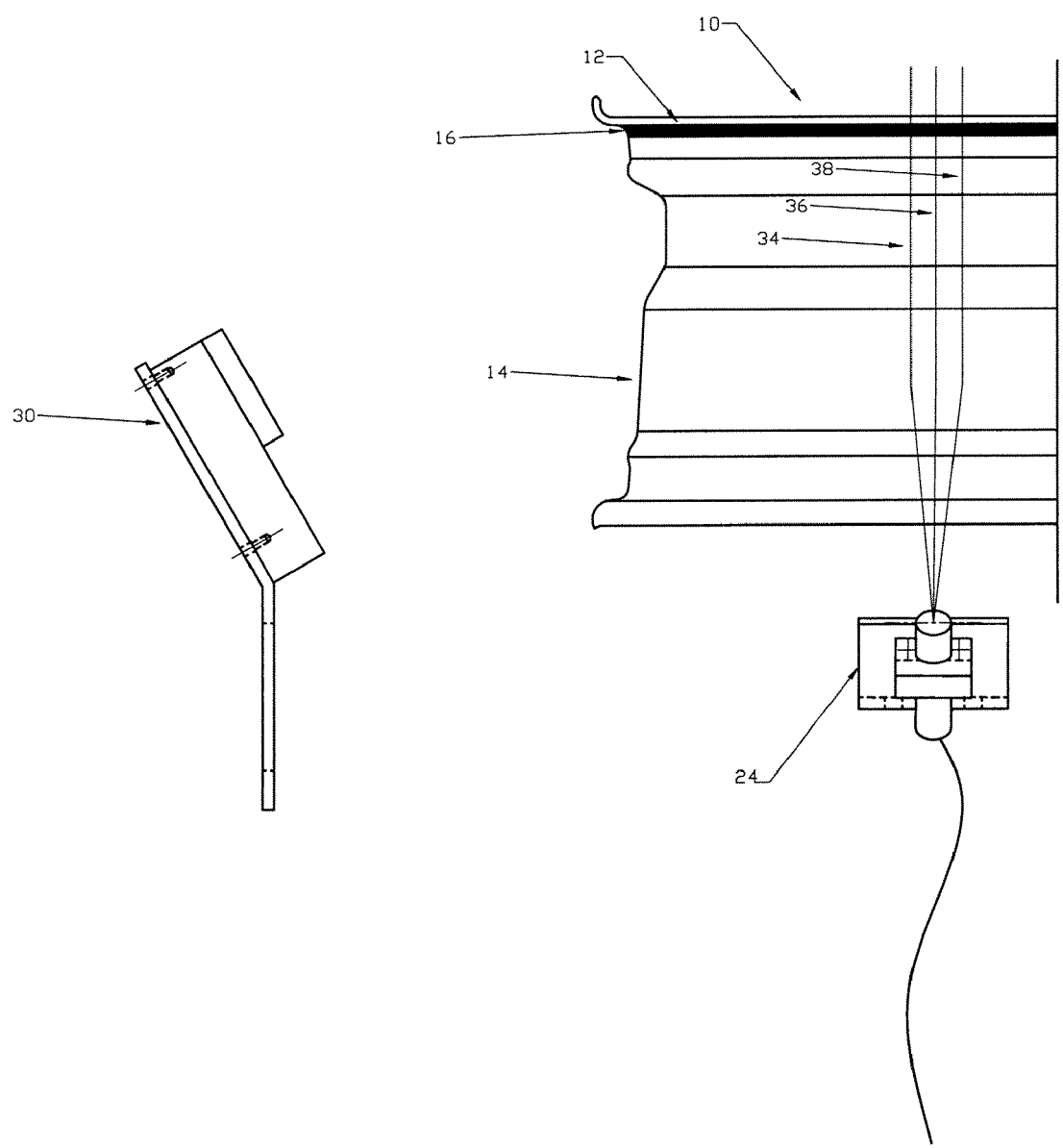

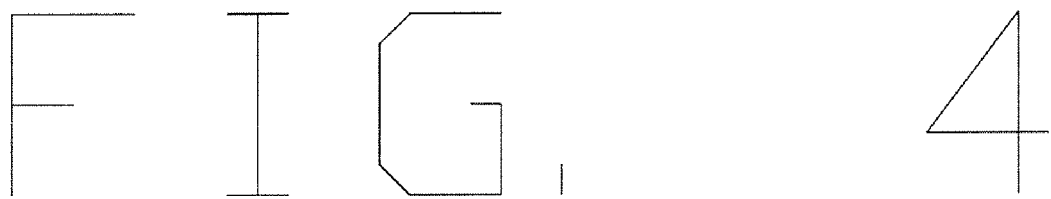
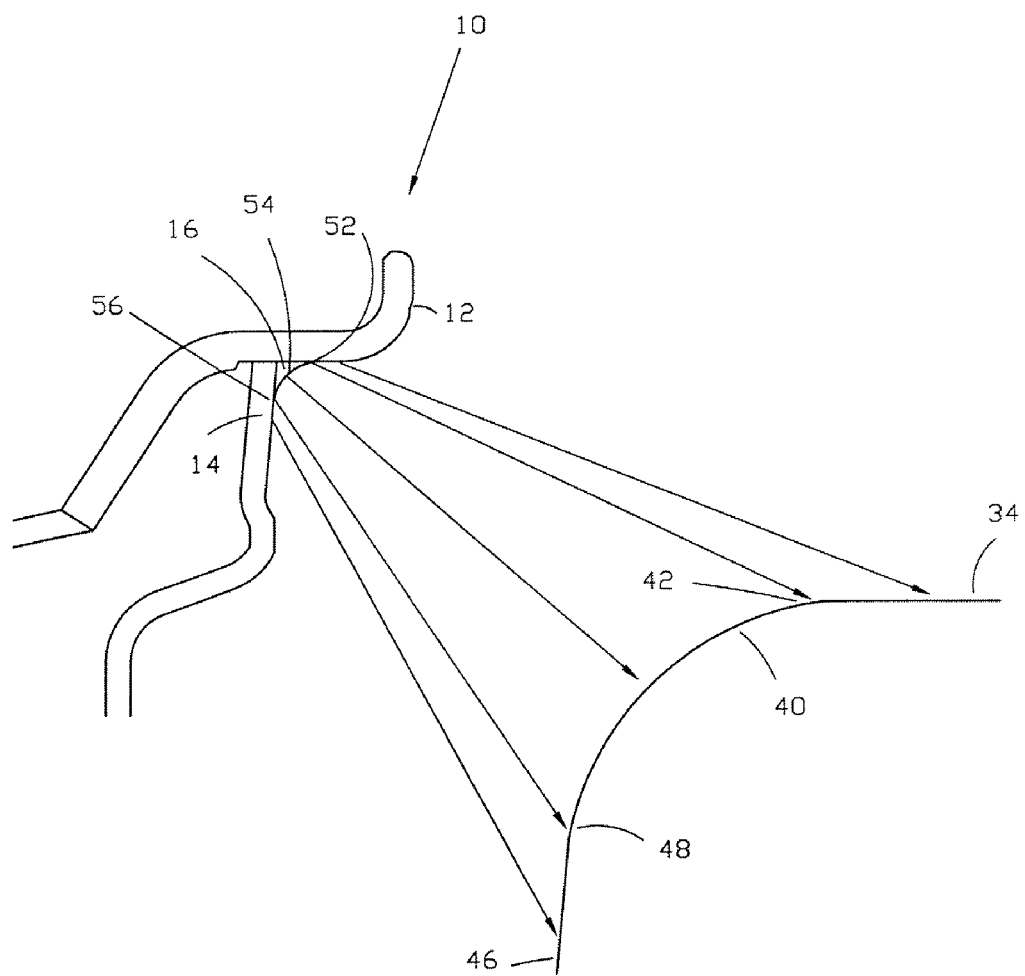

METHOD AND APPARATUS FOR INSPECTING AND ANALYZING WELDED STRUCTURES

BACKGROUND

Relating broadly to equipment for testing the integrity of welds that join two or more structures together in a predetermined relationship and, more particularly, to a method and apparatus for inspection and analyzing such a welded structure utilizing a laser and camera for inspection and to generate a signal as a result of the inspection, a microprocessor is used for analyzing the results of the inspection based on the signal generated by the camera and laser apparatus.

Welding is a fabrication process wherein two or more materials, usually metal or plastic, are joined by melting a portion of the workpieces and adding a filler material to form a pool of molten metal (or other workpiece material) known as the weld puddle that cools to become a strong joint. In industrial and manufacturing settings, robotic welding has become commonplace wherein machines position the work pieces for welding and a robotic welder applies the heat and material necessary to form the weld puddle.

As may be expected, the integrity of the subsequent weld depends, among other things, on the positioning of the work pieces in relation to the position of the welder or heat source. In addition, the positioning of the filler material can also affect the quality and integrity of the subsequent welded joint. In the case of manual welding, the welder can adjust the position of the various materials in order to achieve what he or she feels is the best weld possible. Even then, a more precise inspection process could be useful. With robotic welding, when the machines have no independent capability to determine where to position the materials, other than their preprogrammed positions, certain tolerances may lapse and the weld may not be as good as it can be and, in fact, maybe dangerous with no one becoming the wiser until farther down the manufacturing process, if then.

Accordingly, there exists a need for a welding system that provides an inspection and analysis process directed to the finished weld joint. Further, it is desirable to have such a method and apparatus that is applicable to virtually any welding process but is more particularly directed to welding vehicle wheels.

Typically, during the manufacture of vehicle wheels such as those for automobiles and pickup trucks, the wheel is a two-piece unit having a wheel body, or rim joined to a disc. The wheel is typically mounted to the vehicle while the outer rim carries and seals the tire. As may be expected, such weld joints are extremely important in the safety of vehicle operation when the vehicles are equipped with such wheels. In the case of welded automobile wheels, safety becomes a primary concern because the wheels typically rotate at high rate and support the weight of the vehicle as is it propelled down the road. As can be imagined, catastrophic weld failure can have devastating results.

It would therefore be helpful to have a method and apparatus for inspecting weld joints in wheels. Further, it would be beneficial to provide a method and apparatus whereby qualitative analysis can be performed on the weld joint to use an analysis of the entire welding process.

MULTIPLE EMBODIMENTS

A method and apparatus is provided for inspecting and analyzing weld structures along the junction of wheel discs and wheel rims to determine the integrity of the weld bead or junction based on predetermined weld tolerances.

Such a method and apparatus is provided that can be performed utilizing a microprocessor-based optical analysis.

To these and other ends, an embodiment includes an apparatus for inspecting and analyzing welded structures including a laser for directing at least one beam of light at a weld bead formed on at least two workpieces joined by the weld bead in a predetermined manner to define at least one visible profile line, with the at least one profile line extending along at least a portion of each of the workpieces and along a full dimension of the weld bead. Also included is a camera directed at the weld bead for capturing an image of the at least one laser light beam forming the at least one profile line and generating a usable image signal based on the image.

Also included is a preprogrammed microprocessor assembly configured for receiving the usable image signal and processing the signal as an image. The microprocessor assembly analyzes the image to determine the extent of a predetermined dimension of the weld bead. This is accomplished during processing by the microprocessor assembly being configured for locating at least one profile line on the image; locating the weld bead along the at least one profile line; determining a dimension of the weld bead defined along the at least one profile line; and comparing the dimension of the weld bead with a predetermined dimension set point to determine the quality of the weld bead.

It is preferred that the apparatus for inspecting and analyzing welded structures include the preprogrammed microprocessor assembly being configured for locating a first straight portion of the at least one profile line extending for a predetermined length without curving on the image to identify a first workpiece portion; determining a weld start point by determining where the first straight portion of the at least one profile line begins to curve; defining a first weld dimension line extending tangent to the at least one profile line at the weld start point; locating a second straight portion of the at least one profile line extending for a predetermined length without curving on the image to identify a second workpiece portion; determining a weld bead endpoint by determining where the second straight portion of the at least one profile line begins to curve; defining a second weld dimension line extending tangent to the at least one profile line at the weld bead endpoint, wherein the first and second weld bead lines intersect at a weld bead midpoint; and determining a dimension of the weld bead defined as the sum of a distance from the weld start point to the weld bead midpoint and a distance from the weld bead midpoint to the weld endpoint.

It is further preferred that the first workpiece is a wheel disc and the second workpiece is a wheel rim, and the laser is configured for producing at least one profile line directed laterally across the wheel disc and the wheel rim and a junction thereof. Preferably, the laser produces three generally parallel profile lines and the microprocessor assembly calculates a weld dimension as determined from an average of the results obtained from the three profile lines.

It is preferable that the present apparatus for inspecting and analyzing welded structures is further configured to perform measurements of weld dimension at a plurality of positions along the workpieces. More particularly, it is preferred that the apparatus is configured to perform measurements of weld dimension at twelve positions disposed around the wheel rim and the wheel disc.

It is further preferred that microprocessor assembly is configured to compare the weld dimension with at least two separate set points representing at least two separate failure modes to determine the quality of the weld bead.

According to another, more detailed recitation, an apparatus is provided for inspecting and analyzing welded wheel structures including a laser for directing at least one beam of light at a weld bead formed on at least two workpieces comprising a wheel disc and a wheel rim joined by the weld bead in a predetermined manner to define at least one visible profile line, the at least one profile line extending along at least a portion of each of the wheel disc and the wheel rim and along a full dimension of the weld bead. Also included is a camera directed at the weld bead for capturing an image of the at least one laser light beam forming the at least one profile line and generating a usable image signal based on the image.

Further included is a preprogrammed microprocessor assembly configured for receiving the usable image signal and processing the signal as an image. The microprocessor assembly analyzes the image to determine the extent of a dimension of the weld bead. This is accomplished during processing by the microprocessor assembly being configured for locating at least one profile line on the image; locating the weld bead along the at least one profile line; determining a dimension of the weld bead defined along the at least one profile line; and comparing the dimension of the weld bead with a predetermined dimension set point to determine the quality of the weld bead.

It is preferred that the apparatus for inspecting and analyzing welded structures include the preprogrammed microprocessor assembly being configured for locating a first straight portion of the at least one profile line extending for a predetermined length without curving on the image to identify a wheel disc portion; determining the weld start point by determining where the first straight portion of the at least one profile line begins to curve; defining a first weld dimension line extending tangent to the at least one profile line at the weld start point; locating a second straight portion of the at least one profile line extending for a predetermined length without curving on the image to identify a wheel rim portion; determining a weld endpoint by determining where the second straight portion of the at least one profile line begins to curve; defining a second weld dimension line extending tangent to the at least one profile line at the weld bead end position, wherein the first and second weld bead lines intersect at a weld bead midpoint; and determining a dimension of the weld bead defined as the sum of a distance from the weld start point to the weld bead midpoint and a distance from the weld bead midpoint to the weld endpoint.

Preferably, the laser is configured to produce at least one profile line directed laterally across the wheel disc and the wheel rim and a junction thereof. It is further preferred that the laser is configured to produce three generally parallel profile lines and the microprocessor assembly is configured to calculate a weld dimension as determined from an average of the results obtained from the three profile lines.

Preferably, the apparatus is configured to perform measurements of weld dimension at a plurality of positions around the wheel disc and the wheel rim. More particularly, an embodiment of the apparatus is configured to perform measurements of weld dimension at twelve positions disposed around the wheel rim and the wheel disc.

It is preferable that the microprocessor assembly is configured to compare the dimension of the weld bead with at least two separate set points to determine the quality of the weld bead.

Also provided is a method for using the present apparatus. The method for inspecting and analyzing welded structures includes the steps of:

providing a laser for directing at least one beam of light at a weld bead formed on at least two workpieces joined by the weld bead in a predetermined manner;

defining at least one visible profile line using the laser, the at least one profile line extending along at least a portion of each workpiece and along a full dimension of the weld bead;

providing a camera directed at the weld bead;

capturing an image, using the camera of the at least one laser light beam forming the at least one profile line and generating a usable image signal based on the image; and providing a preprogrammed microprocessor assembly configured for receiving the usable image signal and processing the signal as an image to determine the quality of the weld bead, the processing including the steps of;

locating at least one profile line on the image;

locating the weld bead along the at least one profile line;

determining a dimension of the weld bead defined along the at least one profile line; and comparing the dimension of the weld bead with a predetermined dimension set point to determine the quality of the weld bead.

It is preferred that the present method include the following processing steps using the preprogrammed microprocessor assembly:

locating a first straight portion of the at least one profile line extending for a predetermined length without curving on the image to identify a first workpiece portion;

determining where a weld bead start point is by determining where a first straight portion of the at least one profile line begins to curve;

defining a first weld dimension line extending tangent to the at least one profile line at the weld start point;

locating a second straight portion of the at least one profile line extending for a predetermined length without curving on the image to identify a second workpiece portion;

determining a weld endpoint by determining where the second straight portion of the at least one profile line begins to curve;

defining a second weld dimension line extending tangent to the at least one profile line at the weld endpoint, wherein the first and second weld bead lines intersect at a weld bead midpoint; and determining a dimension of the weld bead defined as the sum of a distance from the weld start point to the weld bead midpoint and a distance from the weld bead midpoint to the weld endpoint.

Preferably, of the at least two workpieces, the first workpiece is a wheel disc and the second workpiece is a wheel rim, and the step of defining at least one profile line includes defining at least one profile line directed laterally across the wheel disc and the wheel rim and a junction thereof. More particularly, it is preferred that the step of defining at least one profile line includes defining three generally parallel profile lines and that the step of determining the dimension of the weld bead includes determining a weld dimension from an average of the results obtained from the three profile lines.

It is further preferred that the method steps are repeated to perform measurements of weld dimension at a plurality of positions along the workpieces. More particularly, in a preferred embodiment, the method steps are repeated to perform measurements of weld dimension at twelve positions disposed around the wheel rim and the wheel disc.

A preferred embodiment provides a method for inspecting and analyzing welded structures wherein the step of comparing the dimension of the weld bead with at least one predetermined set point includes comparing the dimension of the weld bead with at least two separate set points to determine the quality of the weld bead. Furthermore, the step of comparing the dimension of the weld bead with at least two separate set points includes comparing the dimension of the weld bead to a first set point representing a welding torch position and a second set point representing a position of the workpieces to determine quality of the weld bead.

BRIEF DESCRIPTION OF THE DRAWINGS

FIG. 3 is a side view of a wheel rim illustrating the relationship of the laser and camera;

FIG. 4 is a diagrammatic representation of a profile line generated by the laser in relation to the wheel portions and weld structure;

DESCRIPTION OF THE PREFERRED EMBODIMENT

Figure 1:
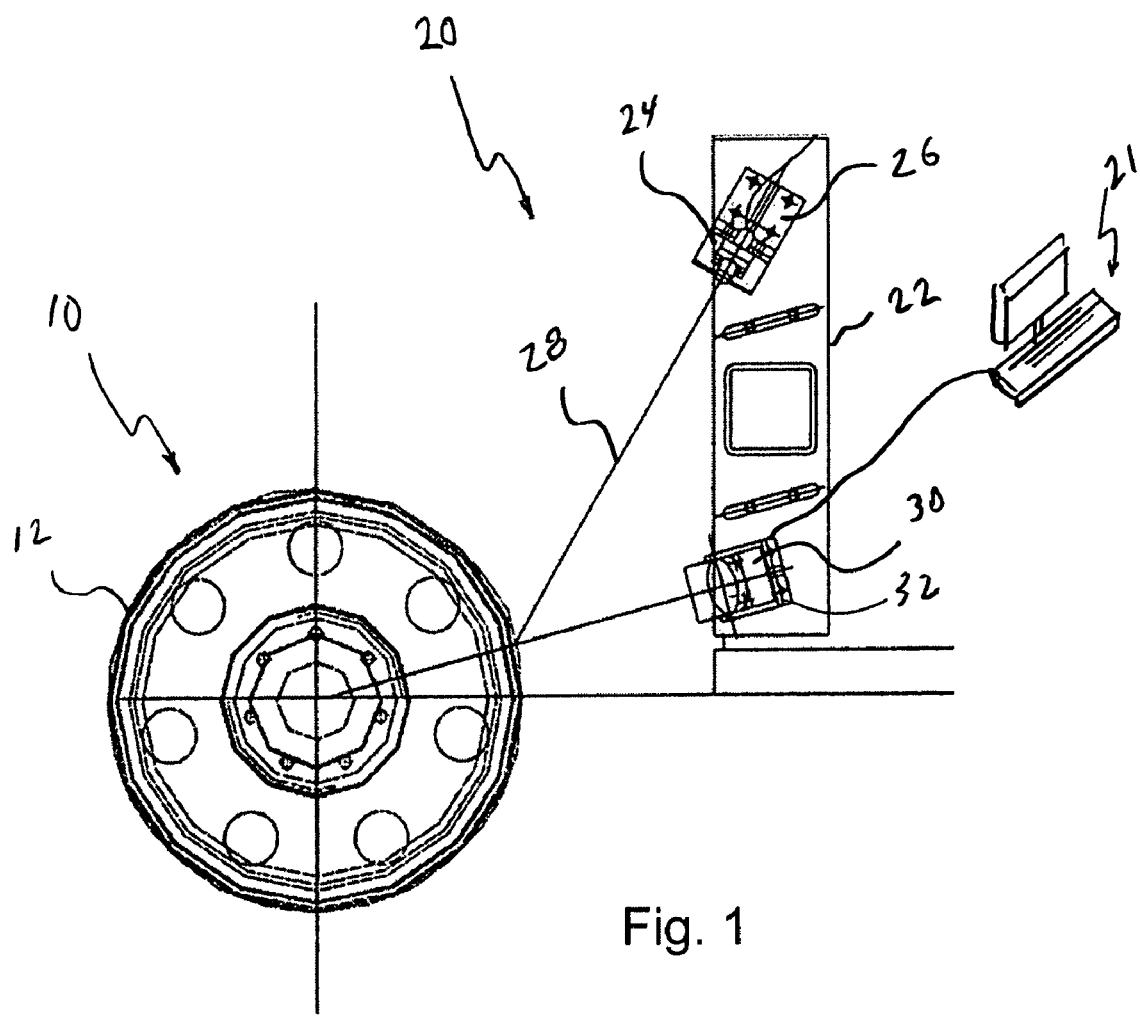
FIG. 1 is a diagrammatic representation of a method and apparatus for inspecting and analyzing welded structures according to one preferred embodiment of the present invention.
Figure 2:
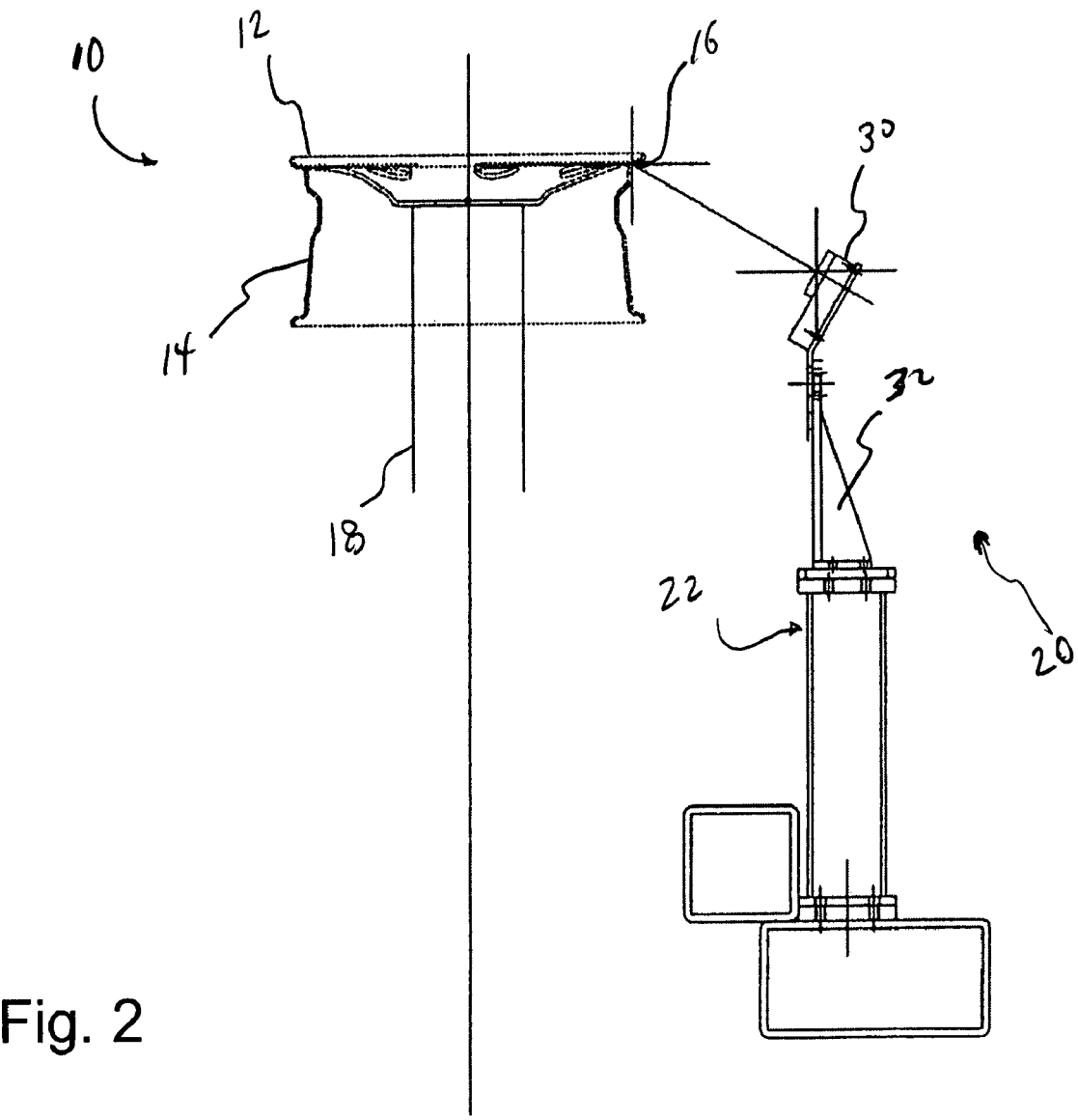
FIG. 2 is a side view of the apparatus illustrated in FIG. 1.

Turning now to the drawings and more particularly to FIG. 1, a wheel structure or wheel assembly is illustrated generally at 10 and includes a wheel disc 12 and a wheel rim 14 as seen in FIG. 2. The wheel 10 is formed by machining the disc 12 and the rim 14 out of, for example, a metal of choice such as, for example, steel, aluminum or some other material. The disc 12 is fitted to the rim 14 with four tack welds. A welder, preferably robotic (not shown) is then employed to apply a weld bead 16 continuously and circumferentially about the junction between the rim 14 and the disc 12. In order to position the wheel 10 for use by an embodiment, a wheel support structure 18 is provided.

With continued reference to FIGS. 1 and 2, an apparatus 20 for inspecting and analyzing the welded wheel structure 10 includes a laser 24, a camera 30 and a microprocessor 21. The laser 24 and camera 30 are supported on a frame structure 22 and each is supported by its own support tower with the camera 30 being supported by a camera support tower 32 and the laser 24 being supported by a laser support tower 26. The microprocessor 21 may be one of a variety of microprocessors to include computers such as, for example, a production line computer or even a personal computer such as, for example, a laptop. The calculations necessary to determine the quality of a weld bead 16 and to otherwise perform the method of the present embodiments are not so complex as to require a great deal of computing capacity. Nevertheless, it is presumed that the microprocessor 21 will be somewhat remote from the laser 24 and camera 30. The microprocessor 21 is in electrical communication with the camera 30 in order to receive and process an image from the camera 30.

The laser 24 is configured for generating and directing a laser beam 28 to a predetermined set point on the wheel assembly 10, forming a profile line 34. As shown in FIG. 3, it is preferred that the laser apply three profile lines, 34, 36, 38, which will be explained in greater detail hereinafter, and that when the wheel 10 is mounted on a wheel support stand 18 such that the disc is oriented, for example, generally horizontal (See FIG. 2), the profile lines 34, 36, and 38 extend vertically up the wheel rim 14 and across the disc 12. The camera 30 is aimed in such a manner as to capture the image of the profile lines 34, 36, 38, as shown in FIGS. 4 and 5.

In operation, and referring back to FIGS. 1 and 2, a laser beam 28 is transmitted from the laser 24 thereby projecting a beam of light on the wheel assembly 10 mounted to the wheel support 18. Referring to FIG. 3, such projection results in three profile lines 34, 36, 38 being projected along the rim 14, the weld bead 16, and the disc 12. The image of the profile lines 34, 36, 38 is captured by the camera 30 for analysis by the microprocessor 21. If displayed on a screen, the profile lines 34, 36, 38 would appear generally as shown in FIGS. 4 and 5. The microprocessor 21 is employed to analyze the profile lines to determine the beginning and end of the weld points on the weld bead 16. FIG. 4 illustrates the correspondence between the wheel assembly 10 and the first profile line 34.

Turning first to the wheel assembly 10, the weld bead 16 includes a wheel disc portion 52 and a wheel rim portion 56 as well as a weld bead midpoint 54. Arrows indicate that on the profile line 34, a location on the disc portion 12 prior to the weld bead 16 is illustrated at 40 and is formed as a straight line. Where the line begins to curve is the rim curve point 42 and which also corresponds to the wheel disc portion 52. For the rim side, a straight portion of the profile line illustrated at 46 represents a location on the rim 14, prior to the weld bead 16. Where the rim line portion 46 of the profile line 34 begins to curve at 48 corresponds to the wheel rim portion 56 of the weld bead 16.

Figure 5:
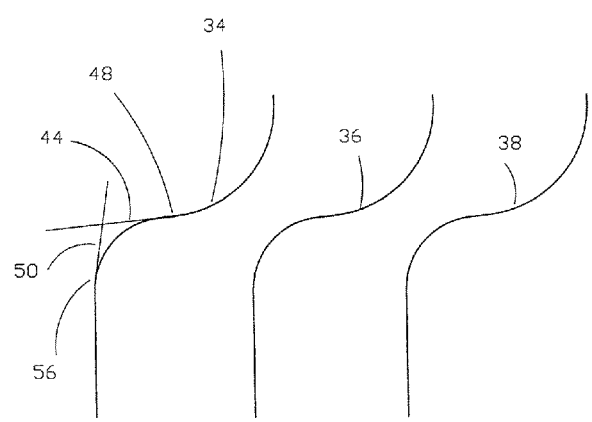
FIG. 5 is a diagrammatic representation of the profile lines as used in analysis by the processor of the present invention.

As shown in FIGS. 4 and 5, and as a part of the automated microprocessor analysis, a line 44 tangent to the rim curve point 42 is drawn by the microprocessor 21. Similarly, a line 50 tangent to the wheel rim portion 56 is drawn. These lines intersect at the weld bead midpoint 54 as illustrated in FIG. 4. The length of the lines 44, 50 is the value of concern regarding the dimension of the weld bead 16. The length is of concern because its analysis can determine the quality of the weld bead 16. Each line 44, 50 is measured and each of the two length measurements for line 44 and line 50, respectively, are compared to set points which are found to be in a range corresponding to the specifications of various customers. The microprocessor 21 determines a first length from profile line 34 and then performs the same activities on the remaining profiles lines 36, and 38, then averages the three results to achieve an average length of the weld bead 16 at the first point of measurement. Preferably, the microprocessor 21 performs this process both for the rim 14 side of the weld 16, and again for the disc 12 side of the weld 16. The microprocessor 21 outputs the resulting averaged length for the rim 14 side and the microprocessor 21 also outputs the resulting averaged length for the disc 12 side, and both lengths are compared to the customer specifications.

According to the method provided, the measurement is taken at multiple positions or locations, and in a preferred embodiment, at 12 positions or locations spaced equally about the wheel assembly 10 in order to obtain representative samples of the circumferential continuous weld bead 16 around the rim 14 and disc 12 juncture of the wheel assembly 10.

It should be noted that the provided weld inspection system should be calibrated using a known weld bead 16 of predetermined size to ensure that the measurements taken from the profile lines 34, 36 and 38 by the microprocessor 21 are valid. It will be apparent to those skilled in the art that calibrating the system in order to achieve accurate results using the present system is well within the skills of one possessing ordinary skill in the art. Therefore, in-depth discussions of the calibration of the system are beyond the scope of the present embodiments.

Analysis has determined that there are two failure modes of the weld bead 16 that are readily identified in the eventuality of two maladjustments of the welding assembly.

The first failure mode occurs if a robotic torch (not shown) is maladjusted and thereby out of position; either more to the rim 14 side or more to the disc 12 side, whereby the quality of the weld bead and accordingly, its measured dimension or length will be affected. The microprocessor 21 conducts this analysis and determines whether the torch is in the right position and also determines a correction factor for the torch.

The second failure mode occurs if the wheel 10 is maladjusted and thereby out of position. Either the rim 14, the disc 12, or both, may be positioned incorrectly by the support structure 18 during the welding process also giving rise to poor weld bead 16 quality readings as determined by the aforesaid microprocessor 21 analysis. Accordingly, utilizing the present embodiments, at least these two failure modes of a weld bead 16 in a wheel assembly 10 may be measured and analyzed with correction factors applied as necessary to ensure the structural integrity of the rim/disc junction and, accordingly, the structural integrity of the wheel assembly 10. Accordingly, the consistency of the wheels 10 produced by the manufacturing process is enhanced and overall wheel 10 quality is enhanced. It should be noted that the preferred embodiments do not directly inform the user which failure mode has occurred. Instead, the preferred embodiments inform the user if one leg length, for either the rim 12 side or the disc 14 side of the weld bead 16 is too short. Such short lengths correspond directly to the failure modes described above.

In the past, a representative number of wheels 10 would be hand-measured to determine whether or not their welds 16 were within the required parameters as defined by the customer's specifications. For the sake of clarity in further teaching this concept, let us consider the OEM automotive parts supply industry where a particular manufacturing plant may be producing many different varieties of wheels 10 for a variety of customers—being various automobile companies who use the wheels 10 in the final assembly of automobiles. Let us designate "x" as a value corresponding to a particular customer's minimally acceptable weld leg length. Let us also designate "z" as a number larger than "x" and which corresponds to a particular wheel 10 manufacturing plant's preferred weld leg length. Furthermore, let us designate "y" as an acceptable weld leg length which corresponds to a range of numbers that fall in between "x" and "z." In other words, "x" is less than the range "y" which is less than "z." In practice, length values are expressed in millimeters or fractions of an inch, but other measurement systems may also be contemplated. Returning to our example, in the past, a typical representative wheel 10 was measured in four places around the wheel 10. With these embodiments, every wheel 10 can be checked at a plurality of locations and, in a preferred embodiment, every wheel 10 is checked in 12 separate locations on the wheel 10. For accuracy, good results have been obtained when the camera 30 resolution is 0.05 millimeters per pixel, although other resolution settings may work sufficiently without departing from the scope and spirit of the present embodiments.

As an example, let us discuss a typical analysis of weld beads 16 that will cause a wheel 10 to fail testing under the present system and method. Using "x", "y" and "z", it has been determined that the dimension or length of the weld bead 16 should be greater than "x." A wheel 10 is considered marginal and in need of further manual inspection if its weld beads 16 have dimensions less than "z." Typically, such dimensions may be, but are not so limited, expressed as a percentage below "z." For example, if the dimension of the weld bead 16 is found to be in a range of lengths corresponding to "y" that wheel 10 is marginal. A weld bead 16 length of less than "x" is further classified as a bad weld.

Recall that, preferably, the wheel 10 is tested at twelve separate locations around the circumference thereof. The wheel 10 will fail its inspection if four or more inspection locations reveal lengths of weld beads 16 corresponding to "y." In addition, if the testing reveals three marginal, or "y", leg length locations in a row, then the wheel 10 will fail. If any particular location has a weld bead 16 length less than "x", the entire wheel 10 will fail. Wheels 10 that have values of "z" or higher pass inspection but such values correspond to longer time in welding, thereby slowing down the assembly line, and increased use of welding rod and energy at the plant. In other words, once a plant's welding machines provide welds that exceed "z", the plant is at risk of having reduced cost effectiveness, hence another reason why the current embodiments improve the efficiency of wheel 10 manufacturing.

It will be apparent to those skilled in the art that the example is provided to illustrate certain predetermined values operable with the present embodiments or a certain wheel 10. Other wheels 10 may provide different actual measurements and the test results of those wheels 10 may dictate the corresponding failure criteria. Nevertheless, the present example illustrates one use of the present embodiments for inspection of weld beads 16 on wheels 10.

It will therefore be readily understood by those persons skilled in the art that the present embodiments encompass a broad utility and application. While the present embodiments are described in all currently foreseeable manners, there may be other, unforeseeable embodiments and adaptation, as well as variations, modifications and equivalent arrangements, which do not depart from the substance or scope of the present embodiments. The foregoing disclosure is not intended or to be construed to limit the present embodiments or otherwise to exclude such other embodiments, adaptations, variations, modifications and equivalent arrangements, the embodiments provided herein being limited only by the claims appended hereto and the equivalents thereof.

We claim:

1. An apparatus for inspecting and analyzing welded structures comprising:
   a laser for directing at least one beam of light at a weld bead formed on at least two workpieces joined by said weld in a predetermined manner to define at least one visible profile line, said at least one profile line extending along at least a portion of each workpiece and along a full dimension of said weld bead;
   a camera directed at said weld bead for capturing an image of said at least one laser light beam forming said at least one profile line and generating a usable image signal based on said image; and
   a preprogrammed microprocessor assembly configured for:
     receiving said usable image signal and processing said signal as an image;
   locating at least one profile line on said image;
   locating said weld bead along said at least one profile line;
   determining a dimension of said weld bead defined along said at least one profile line;
   comparing said length of said weld bead with a predetermined dimension set point to determine the quality of said weld bead;

locating a first straight portion of said at least one profile line extending for a predetermined distance without curving on said image to identify a first workpiece portion;

determining a weld start point by determining where said first straight portion of said at least one profile line begins to curve;

defining a first weld dimension line extending tangent to said at least one profile line at said weld start point;

locating a second straight portion of said at least one profile line extending for a predetermined distance without curving on said image to identify a second workpiece portion;

determining a weld bead endpoint by determining where said second straight portion of said at least one profile line begins to curve; and defining a second weld dimension line extending tangent to said at least one profile line at said weld bead endpoint, wherein said first and second weld bead lines intersect at a weld bead midpoint.

2. An apparatus for inspecting and analyzing welded structures according to claim 1 wherein said preprogrammed microprocessor assembly is further configured for:

determining a dimension of said weld bead defined as the sum of a distance from said weld start point to said weld bead midpoint and a distance from said weld bead midpoint to said weld bead endpoint.

3. An apparatus for inspecting and analyzing welded structures according to claim 1 wherein said first workpiece is a wheel disc and said second workpiece is a wheel rim, and wherein said laser is configured to produce at least one profile line directed laterally across said wheel disc and said wheel rim and a junction thereof.

4. An apparatus for inspecting and analyzing welded structures according to claim 1 wherein said laser is configured to produce three generally parallel profile lines and said microprocessor assembly is configured to determine a weld dimension as determined from an average of the results obtained from said three profile lines.

5. An apparatus for inspecting and analyzing welded structures according to claim 1 wherein said apparatus is configured to perform measurements of weld dimension at a plurality of positions along said workpieces.

6. An apparatus for inspecting and analyzing welded structures according to claim 2 wherein said apparatus is configured to perform measurements of weld dimension at twelve positions disposed around said wheel rim and said wheel disc.

7. An apparatus for inspecting and analyzing welded structures according to claim 1 wherein said microprocessor assembly is configured to compare said weld bead dimension with at least two separate set points to determine quality of said weld bead.

8. An apparatus for inspecting and analyzing welded wheel structures comprising:

a laser for directing at least one beam of light at a weld bead formed on at least two workpieces comprising a wheel disc and a wheel rim joined by said weld bead in a predetermined manner to define at least one visible profile line, said at least one profile line extending along at least a portion of each of said wheel disc and said wheel rim and along a full dimension of said weld bead;

a camera directed at said weld bead for capturing an image of said at least one laser light beam forming said at least one profile line and generating a usable image signal based on said image; and a preprogrammed microprocessor assembly configured for:

receiving said usable image signal and processing said signal as an image;

locating at least one profile line on said image;

locating said weld bead along said at least one profile line;

determining a dimension of said weld bead defined along said at least one profile line;

comparing said dimension of said weld bead with a predetermined dimension set point to determine quality of said weld bead;

locating a first straight portion of said at least one profile line extending for a predetermined length without curving on said image to identify a wheel disc portion;

determining a weld start point by determining where said first straight portion of said at least one profile line begins to curve;

defining a first weld dimension line extending tangent to said at least one profile line at said weld start point;

locating a second straight portion of said at least one profile line extending for a predetermined length without curving on said image to identify a wheel rim portion;

determining a weld bead end point by determining where said second straight portion of said at least one profile line begins to curve; and defining a second weld dimension line extending tangent to said at least one profile line at said weld bead end point, wherein said first and second weld bead lines intersect at a weld bead midpoint.

9. An apparatus for inspecting and analyzing welded structures according to claim 8 wherein said preprogrammed microprocessor assembly is further configured for:

determining a dimension of said weld bead defined as the sum of a distance from said weld start point to said weld bead midpoint and a distance from said weld bead midpoint to said weld endpoint.

10. An apparatus for inspecting and analyzing welded structures according to claim 8 wherein said laser is configured to produce at least one profile line directed laterally across said wheel disc and said wheel rim and a junction thereof.

11. An apparatus for inspecting and analyzing welded structures according to claim 1 wherein said laser is configured to produce three generally parallel profile lines and said microprocessor assembly is configured to calculate a weld dimension as determined from an average of the results obtained from said three profile lines.

12. An apparatus for inspecting and analyzing welded structures according to claim 8 wherein said apparatus is configured to perform measurements of weld dimension at a plurality of positions disposed around said wheel disc and said wheel rim.

13. An apparatus for inspecting and analyzing welded structures according to claim 8 wherein said apparatus is configured to perform measurements of weld dimension at twelve positions disposed around said wheel disc and said wheel rim.

14. An apparatus for inspecting and analyzing welded structures according to claim 8 wherein said microprocessor assembly is configured to compare a weld bead dimension with at least two separate set points to determine quality of said weld bead.

15. A method for inspecting and analyzing welded structures comprising the steps of:

providing a laser for directing at least one beam of light at a weld bead formed on at least two workpieces joined by said weld bead in a predetermined manner;

defining at least one visible profile line using said laser, said at least one profile line extending along at least a portion of each said workpiece and along a full dimension of said weld bead;

providing a camera directed at said weld bead;

capturing an image, using said camera of said at least one laser light beam forming said at least one profile line and generating a usable image signal based on said image; and providing a preprogrammed microprocessor assembly configured for receiving said usable image signal and processing said signal as an image to determine quality of said weld bead, said processing including the steps of:

locating at least one profile line on said image;

locating said weld bead along said at least one profile line;

determining a dimension of said weld bead defined along said at least one profile line;

comparing said dimension of the weld bead to a predetermined dimension set point to determine quality of said weld bead;

locating a first straight portion of said at least one profile line extending for a predetermined length without curving on said image to identify a first workpiece portion;

determining a weld start point by determining where said first straight portion of said at least one profile line begins to curve;

defining a first weld dimension line extending tangent to said at least one profile line at said weld start point;

locating a second straight portion of said at least one profile line extending for a predetermined length without curving on said image to identify a second workpiece portion;

determining a weld end point by determining where said second straight portion of said at least one profile line begins to curve; and defining a second weld dimension line extending tangent to said at least one profile line at said weld end point, wherein said first and second weld bead lines intersect at a weld bead midpoint.

16. A method for inspecting and analyzing welded structures according to claim 15 and further comprising the following processing steps using said preprogrammed microprocessor assembly:

determining a dimension of said weld bead defined as the sum of a distance from said weld start point to said weld bead midpoint and a distance from said weld bead midpoint to said weld bead end point.

17. A method for inspecting and analyzing welded structures according to claim 15 wherein said at least two workpieces further comprise a first workpiece being a wheel disc and a second workpiece being a wheel rim, and wherein said step of defining at least one profile line includes defining at least one profile line directed laterally across said wheel disc and said wheel rim and a junction thereof.

18. A method for inspecting and analyzing welded structures according to claim 15 wherein said step of defining at least one visible profile line includes defining three generally parallel profile lines and said step of determining a dimension of said weld bead includes determining a weld dimension from an average of results obtained from said three profile lines.

19. A method for inspecting and analyzing welded structures according to claim 15 wherein said method steps are repeated to perform measurements of weld dimension at a plurality of positions along said workpieces.

20. A method for inspecting and analyzing welded structures according to claim 15 wherein said method steps are repeated to perform measurements of weld dimension at twelve positions disposed around said wheel rim and said wheel disc.

21. A method for inspecting and analyzing welded structures according to claim 15 wherein said step of comparing said dimension of said weld bead with at least one predetermined set point includes comparing said dimension of said weld bead with at least two separate set points to determine quality of said weld bead.

22. A method for inspecting and analyzing welded structures according to claim 21 wherein said step of comparing said dimension of said weld bead with at least two separate set points includes comparing said dimension of said weld bead to a first set point representing a welding torch position and a second set point representing a position of said workpieces to determine quality of said weld bead.

* * * * *